US007270990B2

(12) United States Patent
Williams et al.

(10) Patent No.: US 7,270,990 B2
(45) Date of Patent: Sep. 18, 2007

(54) VIRUS PRODUCTION (75) Inventors: Gregory V. Williams, Mississauga (CA); Kenneth Hughes, Toronto (CA)

(73) Assignee: Microbix Biosystems, Inc., Ontario (CA)

( * ) Notice: Subject to any disclaimer, the term of this patent is extended or adjusted under 35 U.S.C. 154(b) by 100 days.

(21) Appl. No.: 10/871,768

(22) Filed: Jun. 18, 2004

(65) Prior Publication Data

US 2005/0186223 A1    Aug. 25, 2005

Related U.S. Application Data

(60) Provisional application No. 60/572,718, filed on May 20, 2004, provisional application No. 60/540,782, filed on Jan. 30, 2004, provisional application No. 60/479,723, filed on Jun. 20, 2003.

(51) Int. Cl.
*C12P 21/04* (2006.01)
*C12P 19/34* (2006.01)
*C12N 7/02* (2006.01)
*C12N 5/06* (2006.01)
*C12N 5/00* (2006.01)

(52) U.S. Cl. .................. 435/239; 435/70.3; 435/91.33; 435/349; 435/388; 435/407

(58) Field of Classification Search ................ 435/239, 435/235.1; 424/209.1, 206.1
See application file for complete search history.

(56) References Cited

U.S. PATENT DOCUMENTS

| 3,105,012 | A |   | 9/1963  | Brandon et al. ............... 167/78 |
|-----------|---|---|---------|--------------------------------------|
| 3,316,153 | A |   | 4/1967  | Van Frank .................... 167/78 |
| 3,470,067 | A | * | 9/1969  | Neal et al. ............... 435/173.9 |
| 3,547,779 | A | * | 12/1970 | Lampson et al. ............ 435/239  |
| 3,608,071 | A |   | 9/1971  | Relyveld et al. .............. 424/88 |
| 3,627,873 | A |   | 12/1971 | Moyer ........................ 424/89 |
| 3,632,745 | A |   | 1/1972  | Apostolov .................... 424/89 |
| 3,870,598 | A |   | 3/1975  | Alexeeva et al. ............. 195/1.5 |
| 3,874,999 | A |   | 4/1975  | Zaremba et al. .............. 195/1.5 |
| 3,919,044 | A | * | 11/1975 | Melnick et al. ............. 435/239  |
| 3,962,421 | A |   | 6/1976  | Neurath ....................... 424/89 |
| 4,000,257 | A |   | 12/1976 | Cano ........................... 424/89 |
| 4,057,626 | A |   | 11/1977 | Metzgar et al. ............... 424/89 |
| 4,138,287 | A |   | 2/1979  | Andersson et al. .......... 195/1.5 |
| 4,206,287 | A |   | 6/1980  | Hannoun et al. ............ 435/237  |
| 4,327,182 | A |   | 4/1982  | Benedictus ................... 435/239 |
| 4,338,296 | A |   | 7/1982  | Löbmann et al. .............. 424/89 |
| 4,356,169 | A |   | 10/1982 | Simons et al. ................ 424/89 |
| 4,500,512 | A |   | 2/1985  | Barme ......................... 424/89 |
| 4,500,513 | A |   | 2/1985  | Brown et al. ................. 424/89 |
| 4,724,210 | A | * | 2/1988  | Oka et al. ................... 435/239 |
| 4,783,411 | A |   | 11/1988 | Gabliks ....................... 435/237 |
| 4,808,518 | A | * | 2/1989  | Dorsett et al. ................. 435/5 |
| 5,506,129 | A |   | 4/1996  | Sangar ........................ 435/239 |
| 5,698,433 | A |   | 12/1997 | Kistner et al. ............... 435/239 |
| 5,762,939 | A |   | 6/1998  | Smith et al. ............. 424/210.1  |
| 5,824,536 | A |   | 10/1998 | Webster et al. .......... 435/235.1   |
| 5,948,410 | A |   | 9/1999  | Van Scharrenburg et al. ........................ 424/210.1 |
| 6,008,036 | A |   | 12/1999 | Fanget et al. ................ 435/239 |
| 6,048,537 | A |   | 4/2000  | Violay et al. ............. 424/209.1  |
| 6,146,873 | A |   | 11/2000 | Kistner et al. ........... 435/235.1   |
| 6,210,683 | B1 |  | 4/2001  | Burke et al. ............. 424/230.1   |
| 6,267,967 | B1 |  | 7/2001  | Johnston et al. ......... 424/229.1   |
| 6,344,354 | B1 |  | 2/2002  | Webster et al. .......... 435/235.1   |
| 6,348,197 | B1 |  | 2/2002  | Davelaar ................. 424/214.1   |
| 6,399,357 | B1 |  | 6/2002  | Winge ....................... 435/239  |
| 6,403,363 | B1 |  | 6/2002  | Lawrence et al. ........... 435/260   |
| 6,455,298 | B1 |  | 9/2002  | Gröner et al. ............ 435/235.1   |
| 6,579,528 | B1 |  | 6/2003  | Dowling et al. .......... 424/209.1    |
| 2003/0073223 | A1 | | 4/2003 | Groner et al. ............ 435/235.1   |
| 2003/0087417 | A1 | | 5/2003 | Peeters et al. ............ 435/235.1   |
| 2003/0108918 | A1 | | 6/2003 | Castor et al. ................. 435/6  |
| 2003/0165465 | A1 | | 9/2003 | Roberts et al. ............ 424/93.2   |

FOREIGN PATENT DOCUMENTS

| GB | 660109      |   | 10/1951 |
|----|-------------|---|---------|
| GB | 1140316     |   | 1/1969  |
| GB | WO99/07834  | * | 2/1999  |
| WO | WO97/25415  |   | 7/1997  |
| WO | WO97/37001  |   | 10/1997 |
| WO | WO98/42373  |   | 10/1998 |
| WO | WO99/07834  |   | 2/1999  |
| WO | WO99/18799  |   | 4/1999  |

(Continued)

OTHER PUBLICATIONS

Goyal et al.; Sinple Methods for the Concentration of Influenza Virus from Allantoic Fluid on Microporous Filters; Applied ans Enviromental Microbiology, Mar. 1980, p. 500-504.*
DJS Arora et al.; Concentration and Purification of INfluenza Virus from Allantoic Fluid, Jul. 23, 1984; Analytical Biochemistry 144, 189-192 (1985).*
Wallis et al. Concentration and Purification of Influenza Virus on Insoluble Polyelectrolytes, Applied Microbiology, Apr. 1972, vol. 23, No. 4, pp. 740-744.*
Reimer et al., Purification of Large Quantities of Influenza Virus by Density Gradient Centrifugation, Journal of Virology, Dec. 1967, vol. 1, No. 6, pp. 1207-1216.*

(Continued)

*Primary Examiner*—Bruce R. Campell
*Assistant Examiner*—Sharon Hurt
(74) *Attorney, Agent, or Firm*—Marshall Gerstein & Borun LLP (57) ABSTRACT

An improved process for recovery of virus from allantoic fluid of virus-infected chick embryos. Virus associated with granular and fibrous debris in the allantoic fluid can be disassociated from the debris and recovered, thereby increasing viral yield. Dissociation can be achieved by subjecting the virus-debris complex to conditions of increased salt concentrations, e.g., 0.5 M or greater.

40 Claims, 1 Drawing Sheet

FOREIGN PATENT DOCUMENTS

| | | |
|---|---|---|
| WO | WO 99/28445 | 6/1999 |
| WO | WO99/28445 | 6/1999 |
| WO | WO 99/66045 | 12/1999 |
| WO | WO99/66045 | 12/1999 |
| WO | WO 00/15251 | 3/2000 |
| WO | WO 00/62735 | 10/2000 |
| WO | WO 02/12289 A2 | 2/2002 |
| WO | WO 02/24876 A2 | 3/2002 |
| WO | WO 02/28422 A2 | 4/2002 |
| WO | WO 02/067983 A1 | 9/2002 |
| WO | WO 02/087494 A2 | 11/2002 |
| WO | WO 03/093463 A1 | 11/2003 |

OTHER PUBLICATIONS

Breschkin et al. "Hemagglutination Variant of Measles Virus," *Virology*, 80:441-444 (1997).

Chaloupka et al., "Comparative Analysis of Six European Influenza Vaccines," *Eur. J. Clin. Microbiol. Infect. Dis.*, 15:121-127 (1996).

Dea et al., "Bovine Coronavirus and Cultivation in Continuous Cell Lines," *Am. J. Vet. Res. 41*(1):30-38 (Jan. 1980).

Eggert et al., "Characterization of RNA Polymerase Activity of Highly Purified Preparations of the Influenza Virus A/duck/Alberta/48/76," *Zbl. Bakt. Hyg. A256*:534-.

Floyd et al., "Viral Aggregation: Effects of Salts on the Aggregation of Poliovirus and Reovirus at Low pH," *Appl. Envir. Microbiol.*, 35:1084-1094 (Jun. 1978).

Gaudin et al., "Aggregation of VSV M Protein Is Reversible and Mediated by Nucleation Sites: Implications for Viral Assembly," *Virology*, 206:28-37 (1995).

Götze et al., "Immunogenicity And Partial Purification Of Soluble H-2 Antigens Extracted With Hypertonic Salt," *J. Immunol.*, 112(5):1643-1651 (May, 1974).

Han et al., "pH-dependent Self-association of Influenza Hemagglutinin Fusion Peptides in Lipid Bilayers," *J. Mol. Biol.*, 304:953-965 (2000).

Ikizler et al., "Thermostabilization of egg grown influenza viruses," *Vaccine*, 20:1393-1399 (2002).

James et al., "Safe administration of influenza vaccine to patients with egg allergy," *J. Pediatrics*, 133(5):624-628 (Nov. 1998).

Johnston et al., "Reversible Inhibition of Sindbis Virus Penetration in Hypertonic Medium," *J. Virol.*, 25(1):436-438 (Jan. 1978).

Karakuyumchan et al., "Freeing Rabies Virus Of The Neuroallergenic Factor From Brain Tissue," *Acta virol.*, 25:155-158 (1981).

Lance et al., "Effect of Ionic Composition of Suspending Solution on Virus Adsoption by a Soil Column," *Appl. Envir. Microbiol.*, 47:484-488 (Mar. 1984).

Lukasik et al., "Influence of Salts on Virus Adsorption to Microporous Filters," *Appl. Envir. Microbiol.*, 66(7):2914-2920 (Jul. 2000).

Mabrouk et al., "Influenza vaccine technologies and the use of the cell-culture process (cell-culture influenza vaccine)," *Dev Biol. 110*:125-134 (2002) Abstract.

Makhov et al., "The phenomenon of the conversion of filamentous virions of the influenza virus into spherical particles," (Translation), (*Voprosy Virusologii*, 34(2):274-279 (1989).

Molodkina et al., "Flow ultramicroscopy investigation of the aggregate stability of influenza virus dispersions," *Colloids and Surfaces A:Physicochemical and Engineering Aspects*, 98:1-9 (1995).

Nagy et al., "Purificaton Of Influenza Virus Vaccine Stock Suspension By Ion-Exchange Chromatography," *Acta Microbiologica Academiae Scienitiarum Hungariae*, 25:134-135 (1978).

Oxford et al., "Direct isolation in eggs of influenza A (H1N1) and B viruses with haemagglutinins of different antigenic and amino acid compositions," *J. Gen. Virol.*, 72:185-189 (1991).

Pauli et al., "Increase of virus yields and releases of Borna disease virus from persistently infected cells," *Virus Research*, 2:29-33 (1985).

Robertson et al., "The role of amniotic passage in the egg-adaptation of human influenza virus is revealed by haemagglutinin sequence analyses," *J. Gen. Virol.*, 74:2047-2051 (1993).

Sampson et al., "Relationship between food-specific IgE concentrations and the risk of positive food challenges in children and adolescents," *J. Allergy Clin. Immunol.*, 100(4) (Oct. 1997)—website: www.2.us.elsevierhealth.com/scripts/om.dll/serve.

Sampson, "Food allergy, Part 2: Diagnosis and management," *J. Allergy Clin. Immunol.*, 103(6):981-989 (Jun. 1999).

Sampson, "Utility of food-specific IgE concentrations in predicting symptomatic food allergy," *J. Allergy Clin. Immunol.*, 107(8):891-896 (May 2001).

Shields et al., "Influence of Salts on Electrostatic Interactions Between Poliovirus and Membrane Filters," *Appl. Environ. Microbiol.*, 45:526-531 (Feb. 1983).

Stevely et al., "The Effect Of Hypertonic Conditions On Protein Synthesis In Cells Infected With Herpes Virus," *FEBS Lett.*, 87(2):308-310 (Mar. 1978).

Stigter et al., "Charge Effects on Folded and Unfolded Proteins," *Biochemistry*, 29:1262-1271 (1990).

Eggert et al., "Characterization of RNA Polymerase Activity of Highly Purified Preparations of the Influenza Virus A/duck/Alberta/48/76," *Zbl. Bakt. Hyg. A256*:534-540, 1984.

Voorthuizen et al., "Role of hydrophobic and electrostatic interactions for initial enteric virus retention by MF membranes," *J. Membrane Sci.*, 194:69-79 (2001).

Vogel, "Neutral Salt Effects On The Polymorphism Of Tobacco Mosaic Virus Protein, A Contribution To The Understanding Of Its Mechanism Of Aggregation And Virus Reassembly," *Biochimica Biophys. Acta*, 706:65-79 (1982).

Wallis et al., "Cationic Stabilization—A New Property of Enteroviruses," *Virol.*, 16:504-506 (1962).

Willkommen et al., "The Influence Of pH And Ionic Strength On The Single Radial Immunodiffusion Test In Qualitative Assay Of Influenza Virus Haemagglutinin," *Acta Viol.*, 27:407-411 (1983).

Young et al., "Poliovirus Aggregates and Their Survival in Water," *Appl. Envrion. Microbiol.*, 33:168-177 (Jan. 1977).

Zeiger, "Current issues with influenza vaccination in egg allergy," *J. Allergy Clin. Immunol.*, 110(6):834-840 (Dec. 2002).

Zhang et al., "Characterization of the Membrane Association of the Influenza Virus Matrix Protein in Living Cells," *Virol.*, 225:255-266 (1996).

State of Alaska Epidemiology Bulletin, "Recommendations—Influenza Vaccine 1999-2000," Bulletin No. 13 (Aug. 10, 1999)—www.epi.hss.state.ak.us/bulletins/docs/b1999_13.htm.

Sudnik et al., *Vyestsi Akadmeii Navuk BSSR Syeryya Biyalahichnykh Navuk*, 6:71-77 (1985). (Summary in English)-only summary considered—Article in Russian.

* cited by examiner

FIG. 1

VIRUS PRODUCTION

This application claims priority to U.S. provisional application Ser. No. 60/479,723, filed Jun. 20, 2003, U.S. provisional application Ser. No. 60/540,782, filed Jan. 30, 2004, and U.S. provisional application Ser. No. 60/572,718, filed May 20, 2004, all of which are incorporated by reference in their entirety.

FIELD OF THE INVENTION

The present invention relates to the recovery of enveloped virus from allantoic fluid of virus-infected chick embryos. The heightened recoveries facilitate production of viral vaccines, especially influenza vaccine, and can also provide enhanced yields of viral proteins, including heterologous proteins expressed by viral vectors.

BACKGROUND OF THE INVENTION

Upon infection by a pathogen, the host's immune system recognizes antigens on or in the pathogen and directs an immune response against the antigen-containing pathogen. During this response, there is an increase in the number of immune cells specific to the antigens of the pathogen and some of these cells remain after the infection subsides. The presence of the remaining cells prevents the pathogen from establishing infection when the host is subjected to the pathogen at a later time. This is referred to as protective immunity.

Vaccines provide protective immunity against pathogens by presenting a pathogen's antigens to the immune system without causing disease. Several methods have been developed to allow presentation of antigens without disease-causing infection by the pathogen. These include using a live but attenuated pathogen, an inactivated pathogen, or a fragment (subunit) of the pathogen.

Because therapy for many viral infections remains elusive, it is preferred to prevent or moderate infection through vaccination rather than treat the infection after it occurs. Examples of particularly problematic infectious viruses are those of the orthomyxoviridae, especially influenza virus, paramyxoviridae, flaviviridae, togaviridae, rhabdoviridae, and coronaviridae families. Millions of people are vaccinated against one or more members of these virus families each year.

While some viruses will propagate well in cell culture, others require propagation in embryonated chicken eggs with virus recovery from allantoic fluids. Influenza vaccine has been supplied to the populace for many years as a multi-strain combination product recovered from the allantoic fluids of embryonated chicken eggs. Three strains, selected annually from a large panel of strains, are grown, purified, and pooled to create a given vaccine. The growth of each selected strain of influenza can vary markedly, often leading to difficulties in efficiently meeting the annual market demand for such a trivalent vaccine.

Various methods have been proposed to improve and/or simplify the recovery of virus or viral products from feedstock. U.S. Pat. No. 3,627,873 describes a process in which virus is extracted from concentrated allantoic fluid feedstock using diethyl ether and methylacetate. Still further yield improvements are said to have been obtained using multiple extractions with both butyl and ethylacetates according to U.S. Pat. No. 4,000,257.

U.S. Pat. No. 3,316,153 describes a multi-step extraction process, aimed at separating virus particles from cellular debris and is assertedly applicable to feedstocks that derive from virus-infected chick allantoic fluid or from cell or tissue-culture fluids. In this method, virus adsorbed to precipitated calcium phosphate is dispersed in EDTA at pH 7.8-8.3, causing dissociation and an EDTA-based sequestering of the soluble calcium, thereby releasing the virus for recovery. The resulting virus-containing solution is dialyzed against water or preferably an aqueous glycine-sodium chloride solution to reduce the EDTA and phosphate content.

U.S. Pat. No. 4,724,210 describes methods for purification of influenza using ion exchange chromatography. An influenza-containing solution, e.g. allantoic fluid, is passed through cellulose sulfate column wherein the virus is adhered to the column packing. The column is subsequently washed and virus eluted with a solution containing 1.0 M to 1.5 M sodium chloride. This is followed by a 4.99 M sodium chloride wash.

In WO 02/067983, preparation of a split influenza vaccine is described as involving moderate-speed centrifugation to clarify allantoic fluid, adsorption of the clarified fluid on a $CaHPO_4$ gel, followed by resolublization with an EDTA-$Na_2$ solution. See also WO 02/08749 describing the same process.

In U.S. Pat. No. 4,327,182, allantoic fluid feedstocks from the growth of influenza virus are subjected to a multi-stage extraction process aimed at recovering influenza subunits, haemagglutinin (HA) and neuraminidase (NA). The technique relies on a concentration step in which virus feedstock is present with detergent and a saline solution followed by successive filtration to remove non-viral particles.

U.S. Pat. No. 3,962,421 describes a method for the disruption of influenza viruses. Allantoic fluid is subjected to high-speed centrifugation. The resulting pellet is resuspended in saline and ball-milled for 12-15 hours to create a virus suspension. The virus suspension is then treated with phosphate-ester to disrupt the virus particles into lipid-free particles (subunits) that carry the surface antigens of intact viruses.

In U.S. Pat. No. 3,874,999, allantoic fluids containing influenza virus are centrifuged at low speeds to remove gross particles. The virus is then removed from the supernatant by high-speed centrifugation and resuspended in a phosphate buffer. Nonvirus proteins and lipids are removed by treatment of the suspension with 0.1-0.4 M magnesium sulfate at an alkaline pH for 16-18 hours at 4° C. The resultant suspension is clarified by low speed centrifugation and the virus is purified from the resulting supernatant.

Of particular interest to the background of the invention are viral recovery manipulations involving the contact of non-allantoic fluid virus sources with solutions having elevated concentrations of one or more salts and studies of the effect of various salt concentrations on purified virus.

Some processes assertedly provide for increased yields or greater purity of virus when infected cells are contacted or incubated with solution containing elevated salt concentrations followed by purification of the virus from the solution.

In WO 99/07834, herpesvirus infected Vero cell cultures are incubated in a hypertonic aqueous salt solution (e.g., 0.8 to 0.9 M NaCl) for several hours. The solution is then removed and herpesvirus harvested from the solution. This method was asserted to be superior to methods wherein the cells are subjected to ultrasonic disruption.

Others have addressed contacting virus-infected cultured cells with elevated salt concentrations.

U.S. Pat. No. 5,506,129 reports increased yields of hepatitis A virus after growing infected BS-C-1 cells in growth medium containing ~0.3 M NaCl.

Karakuyumchan et al. (*Acta virol.*:155-158, 1981) reports that rabies virus obtained after shaking infected brain tissue in a 0.3 M NaCl containing buffered solution lacks neuroallergenic activity caused by residual brain tissue.

Pauli and Ludwig (*Virus Research*, 2:29-33, 1985) reports increased yields of Boma disease virus from a virus-infected cell lines grown in medium containing ~0.3 M NaCl.

Various groups have studied the effect of contacting purified viruses with elevated salt concentrations on the characteristics of the virus.

In Breschkin et al. (*Virology*, 80:441-444, 1977), a particular mutated measles virus lacking hemagglutination activity in isotonic saline has wild-type level hemagglutination activity in 0.8 M $(NH_4)_2SO_4$, whereas the high salt has no effect on the hemagglutination activity of a wild-type virus.

Wallis and Melnick (*Virology*, 16:504-506, 1962) report that, while high salt (1 M $MgCl_2$, 1 M $CaCl_2$, or 2 M NaCl) prevents heat inactivation of polio, coxsackie, and ECHO viruses, 1 M $MgCl_2$ enhances inactivation of adeno-, papova-, herpes-, myxo-, arbor, and poxviruses.

In Willkommen et al. (*Acta virol*., 27:407-411, 1983), purified lyophilized influenza virus is reconstituted in buffered saline containing increasing concentrations of NaCl (up to 1.15 M). Subsequently, the reconstituted virus is cleaved with detergent and a single-radial-immunodiffusion (SRD) test performed. With some strains of influenza virus, increasing the salt concentration in the reconstitution buffer shows no effect on the results of an SRD test to hemaggluinin (HA). However, other strains, when reconstituted in buffered saline containing 1.15 M NaCl, give a HA concentration in the SRD test that is twice that of the same strain reconstituted in buffered saline containing 0.15 M NaCl. The authors identify viral aggregation as possibly blocking detergent penetration and attenuated the SRD response.

Molodkina et al. (*Colloids and Surfaces A: Physicochemical and Engineering Aspects*, 98:1-9, 1995) report that increasing salt concentrations up to 0.3 M NaCl leads to dispersion of purified influenza virus aggregates.

Sudnik et al. (*Vyestsi Akademii Navuk BSSR Syeryya Biyalahichnykh Navuk*, 6:71-77, 1985) report high ionicity can partially offset the destruction of the influenza virus envelope at pH 2.2.

Also of interest to the background of the invention are the results of studies by Makhov et al. (*Voprosy Virusologii*, 34(2):274-279, 1989) on the proportion of filamentous influenza virions in allantoic fluids. In a context divorced from virus recovery, Makhov et al. report that presence of filamentous influenza virions in allantoic fluids is strain specific and ionic-strength dependent. Allantoic fluids were examined using electron microscopy to determine the presence of filamentous virions. The occurrence of filamentous virions in the allantoic fluid for one particular influenza strain was 7.1%. When the NaCl concentration was raised to 0.25 M or 1.0 M, the occurrence was reduced to 0.37% and 0.16%, respectively.

Thus, there remains a need in the art for an improvement of the purity and yield of viruses from allantoic fluid of virus-infected chick embryos.

SUMMARY OF THE INVENTION

The invention provides an improvement in a process for recovering virus from allantoic fluid of virus-infected chick embryos. As disclosed herein, a considerable portion of the virus within the allantoic fluid has now been found to be associated with granular or fibrous debris and is therefore lost when the allantoic fluid is clarified to remove the debris. By dissociating the virus from the debris prior to final separatory processing, viral yields are improved.

Processes to recover virus from allantoic fluid often contain a step wherein the allantoic fluid is subjected to clarification, e.g., by centrifugation or filtration, to form a clarified liquid fraction and a debris-containing fraction. When the allantoic fluid is clarified by centrifugation, the debris-containing fraction is typically in the form of a pellet; when clarified by filtration, it is typically in the form of a retentate. By including the step of extracting virus from this debris-containing fraction, the invention provides an improvement over known processes of recovering virus from allantoic fluid of infected chick embryos.

A preferred method of extracting virus the debris-containing allantoic fluid fraction is to dissociate the virus into a suspension having a non-isotonic concentration of one or more salts. In particular, virus is readily dissociated from the debris with solutions comprising one or more salts having a total salt concentration therein of about 0.5 M or greater or equivalent mole ratio of salt per ml of allantoic fluid. Particularly useful solutions are phosphate buffered solutions having a pH ranging from 3 to 10 and comprising a total salt concentration (e.g., total NaCl concentration) from about 1.0 M to about 3.5 M. Dissociated virus can be recovered from the suspension. Recovery can include a second clarification forming a second clarified liquid and a second debris-containing fraction. Preferred methods of recovering virus also include localization of the virus on a sucrose density gradient.

In some aspects, the invention provides a process for recovering virus from allantoic fluid of virus-infected chick embryos by adding one or more salts to the allantoic fluid to generate a total salt concentration therein of about 0.5 M or greater followed by recovering virus from the resulting fluid. The salt can be added in the form of an aqueous solution, such as concentrated phosphate buffered saline (PBS). In one embodiment, the salt is added to the allantoic fluid prior to removing the allantoic fluid from an egg. After addition of the one or more salts, recovery of the virus can include a clarification step to form a debris-containing fraction. Any virus remaining in the debris-containing fraction can be extracted to optimize viral yields. Alternatively, the salt-treated allantoic fluid may be directly processed by, e.g., sucrose density gradient fractionation with or without removal of water to reduce the volume of fluid subjected to fractionation.

In a particularly preferred embodiment, a solution of one or more salts is added to allantoic fluid to generate a total volume concentration therein of about 1.5 M or greater. The pH of the allantoic fluid also can be adjusted or maintained. Preferred ranges of pH include pH 3.0 to pH 6.8 or pH 6.8 to pH 9.8. After the salts are added to the allantoic fluid, it is clarified by centrifugation or filtration. The clarified allantoic fluid is then subjected to sucrose density gradient separation to localize virus. Subsequently, localized virus is isolated from the gradient.

The methods of the present invention can be used to recover essentially any virus that replicates in virus-infected chick embryos and is present in the allantoic fluid. Particularly preferred viruses are the enveloped RNA viruses, including members of the orthomyxoviridae, paramyxoviridae, flaviviridae, togaviridae, rhabdoviridae, and coronaviridae families. As demonstrated in the Examples, methods of the present invention improve the recovery of both Influenza A and Influenza B virus considerably.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

DESCRIPTION OF THE PREFERRED EMBODIMENTS

In one aspect, the invention provides an improved process for recovery of virus from allantoic fluid of virus-infected chick embryos. This process significantly improves the yield of virus from allantoic fluid and provides highly purified virus compositions, or derivative virus subunit preparations, useful to prepare vaccines.

As used herein and in the claims, "virus" shall mean enveloped, preferably intact and infectious, viral particles as opposed to viral fragments, components and/or individual viral antigens such as obtained by well-know splitting techniques. Following recovery of virus according to the present invention, viral particles may readily be subjected to fragmentation or splitting.

Processes of the invention are applicable to both naturally occurring viruses and genetically modified viruses, such as those described, for example, in WO 99/66045 and its counterpart publication US 2003/0087417.

In a preferred embodiment, virally infected allantoic fluid from chick embryos is prepared according to guidelines currently established for vaccine production. Generally, this process entails the use of 9-12 day old embryonated chicken eggs that are pre-candled to eliminate spoiled or unfertilized eggs. The remaining eggs are then inoculated in the amniotic and/or allantoic cavity with the particular strain of live virus for which a vaccine is desired. The eggs are incubated at 32-37° C. typically for two or three days, post-candled to eliminate spoiled eggs, and the eggs are next refrigerated at a temperature of about 4-6° C. for about 24 hours before the egg fluids are aseptically harvested. The allantoic fluid so harvested contains a high concentration of live virus. This process is useful particularly for the production of influenza virus of various types including most or all strains influenza-A and influenza-B.

As demonstrated in Example 1 below, although the virus infected allantoic fluid contains a high concentration of live virus, much of the virus is associated (aggregated) with fibrous or granular debris and is lost when the debris is typically separated from the allantoic fluid by clarification. By employing elevated salt concentrations to dissociate virus from the debris and recovering the dissociated virus, the methods of the present invention provide increased viral yields from allantoic fluid. Virus can be dissociated from the debris within the allantoic fluid (either within the infected egg or after the allantoic fluid is removed from the egg) prior to any clarification. Indeed, in some instances, clarification can be dispensed with as a preliminary recovery step prior to, e.g., sucrose density gradient separation. Alternatively, the allantoic fluid can be clarified to form a debris-containing fraction and the virus can be subsequently dissociated from the debris in this debris-containing fraction. After dissociation from the debris, virus can be recovered using conventional virus purification techniques as described below.

A preferred method of dissociating virus from the aggregated debris is to place the virus associated with the debris in an environment having a non-isotonic salt concentration. The environment is said to have a "non-isotonic" salt concentration when it differs significantly from that of allantoic fluid, which has a total salt concentration of about 150 mM. Examples of non-isotonic salt concentrations include, but are not limited to, 10 mM or less, 20 mM or less, 30 mM or less, 40 mM or less, 50 mM or less, 60 mM or less, 70 mM or less, 80 mM or less, 90 mM or less, 100 mM or less, 110 mM or less, 120 mM or less, 130 mM or less, 140 mM or less, which concentrations can result from dilution of allantoic fluid with water. Dilution with isotonic salt solutions such as phosphate buffered saline will not render the allantoic fluid non-isotonic but, as noted below, may have beneficial effects in terms of dissociating virus from debris.

Non-isotonic salt concentrations includes hypertonic salt concentrations such as 160 mM or greater, 170 mM or greater, 180 mM or greater, 190 mM or greater, 0.2 M or greater, 0.3 M or greater, 0.4 M or greater, 0.5 M or greater, 0.6 M or greater, 0.7 M or greater, 0.8 M or greater, 0.9 M or greater, 1.0 M or greater, 1.1 M or greater, 1.2 M or greater, 1.3 M or greater, 1.4 M or greater, 1.5 M or greater, 1.6 M or greater, 1.7 M or greater, 1.8 M or greater, 1.9 M or greater, 2.0 M or greater, 2.5 M or greater, 3.0 M or greater, and 3.5 M or greater and may be obtained by direct addition of free salt or preferably, by addition of concentrated salt solutions.

In all embodiments, one or more salts are added to the allantoic fluid to accomplish dissociation of virus from the aggregated debris. Once virus dissociation occurs, the virus-containing solution could be diluted, e.g., rendered more isotonic (i.e. less hypertonic) again, prior to recovering the virus. Alternatively, the allantoic fluid can be diluted prior to or concurrently with salt addition and the diluted solution may thereafter be concentrated to increase the salt concentration thereby dissociating virus from the aggregated debris, prior to recovering the virus. In such embodiments, a preferred mole ratio of salt to original volume of allantoic fluid is created.

For example, in illustrative example 10 below, a 100 ml aliquot of allantoic fluid was diluted by the addition of 50 ml of 1×PBS, bringing the sample volume to 150 ml. An equal volume (150 ml) of 20×PBS was subsequently added to the sample to create a final volume of 300 ml. Allantoic fluid and 1×PBS have a NaCl concentration of about 0.15 M (150 mM). Thus, there was 0.015 moles NaCl (0.1 L×150 mM NaCl) in the original allantoic fluid. Then 0.0075 moles NaCl (0.05 L×150 mM NaCl) was added by the dilution with 1×PBS. The addition of the 20×PBS added 0.45 moles NaCl (0.15 L×3.0 M NaCl). The 300 ml final volume contained 0.4725 moles of NaCl (0.015+0.0075+0.45). Therefore, the mole ratio of salt to allantoic fluid was 0.4725 moles per 100 ml allantoic fluid or 4.725 mmoles per ml of allantoic fluid starting material. Had the adjustment of allantoic fluid been to 0.5 M NaCl, the mole ratio would have been 1.5 mmoles NaCl per ml of allantoic fluid starting material, regardless of the adjusted (total) volume.

Preferred salts are those that are generally regarded as safe (GRAS) for use in human pharmaceuticals. The preferred salt is sodium chloride. The salt can also be formed from monovalent, divalent or multivalent cation mixtures thereof and can include or specifically exclude ammonium sulfate.

Thus, KCl, LiCl, $CaCl_2$, $MgCl_2$ and other salts are envisioned as combinations of salts. Other salts include a variety of inorganic salts and organic salts (e.g. sodium acetate, potassium acetate, etc.). In embodiments wherein elevated salts concentrations are used to dissociate virus from the aggregated debris, the salts selected for use in the present method should be those salts which remain soluble at the high concentration required to confer the desired environment. Any salt that can substantially increase the ionicity (osmolarity) of a solution while retaining solubility is suitable. Such salts include sodium chloride and potassium chloride and the like.

In a preferred embodiment, virally infected allantoic fluid prepared in the established manner is admixed with an aqueous solution containing salt at high concentration, so that the resulting admixture contains the salt at a molarity of at least 0.5 M and at most saturation, more desirably at a molarity in the range from 1.0 M to 3.5 M. This can usually be achieved, for instance, by mixing equal volumes of allantoic fluid and salt solution, or using any other blending procedure that provides the desired salt concentration. In certain embodiments, the allantoic fluid can be removed from the egg prior to addition of the salt solution. In other embodiments, salt solution is added to the allantoic fluid within the egg, or used to wash the allantoic chamber after collection of the bulk allantoic fluid.

Preferably, the admixture of allantoic fluid with salt is also buffered, using for instance a phosphate buffering system (e.g., 20-250 mM) in the usual manner to provide a desired pH. A preferred pH range is from 3.0 to 10.0. The pH can be adjusted to maximize the recovery on a virus-by-virus basis. Yields can further be enhanced by tailoring the pH of the concentrated salt/feedstock admixture to within a range preferred for a given virus type or subtype. A preferred pH range is from 3.0 to 10.0. For instance, Moscow strains of Influenza A provide higher yields when the non-isotonic environment has a relatively neutral/slightly acidic pH in the range from 6.8-7.1. However, under the same salt conditions, yields of certain Yamanashi strains of Influenza B are greater when the non-isotonic environment has a higher pH level, about 8.4.

The environment in which the virus is dissociated from debris can further comprise a divalent cation chelating agent, such as EDTA. The chelating agent serves the purpose of sequestering divalent cations that effect precipitation or agglomeration of virus particles, thus rendering them either invisible to the titre measurement or unavailable to the inactivation conditions used during the vaccine production phase of the process. Suitable chelating agent concentrations are those that foster separation of agglomerated virus particles. In the case of EDTA, concentrations suitably are within the range from 1.0 mM to 1.0 M, depending on the initial divalent cation concentration. Other additives, alone or in combination, include reducing agents, such as DTT, and wetting agents, such as the nonionic detergents Triton X-100 and Pluronic F68.

As noted above, in certain embodiments, one or more salts are added to allantoic fluid from virus-infected chick embryos to elevate the salt concentration therein. In certain embodiments, this entails the admixture of allantoic fluid and a concentrated salt solution that is optionally pH adjusted and optionally contains a chelating agent, at room temperature (18-25° C.) for convenience. The admixture can be stirred. The admixture is then chilled to preserve virus infectivity without precipitating the salt and the virus-containing suspension is formed either during a non-agitation resting period or, desirably, by centrifugation or filtration.

The virus-containing supernatant or filtrate is then processed as desired to further enrich for virus. Typically, the supernatant is next subjected, in the manner established for raw allantoic fluid, to a sucrose gradient centrifugation processing that localizes virus on or within the gradient. The localized virus can be recovered from the gradient to yield virus-containing fractions. One or more pooled virus-containing fractions can be obtained following the sucrose-based separation process, to form an enriched virus extract. This enriched virus extract can also be subjected to the high salt treatment, preventing or removing aggregates of virus that are commonly induced by gradient purification.

It is to be appreciated that the present method is not limited to any particular fractionation or separation process, but instead can be applied with any other fractionation or separation processes useful to obtain purified virus from allantoic fluids, including those utilizing size exclusion chromatography, centrifugation, filtration, solvent extraction, ion-exhange chromatography, and the like. Moreover, any one or more of the resulting fractions can be rendered non-isotonic, to improve the virus recovery process, in that virus is rendered substantially monodisperse in solution.

In certain embodiments, the recovered virus is inactivated. The inactivation process can be any of those already established in vaccine production, including formalin fixation, irradiation, detergent or solvent splitting and the like.

The present invention can be applied for the recovery and purification of a wide range of viruses. In preferred embodiments, the method is applied for the recovery of an enveloped virus comprising an RNA genome. Such viruses include those of the family orthomyxoviradae (e.g., influenza viruses), paramnyxoviridae (e.g., mumps virus, Sendai virus, and Newcastle disease virus), flaviviridae (e.g., Japanese encephalitis virus and yellow fever virus), togaviridae (e.g., rubella), rhabdoviridae (e.g., vesicular stomatitis virus and rabies virus), and coronaviridae (e.g., avian infectious bronchitis virus). In particular embodiments, the method is applied for the recovery of influenza virus, including strains of Influenza A, Influenza B, Influenza C, avian influenza virus, equine influenza virus, and swine influenza virus.

As noted above, in certain practices of the invention, the allantoic fluid is diluted prior to recovery of virus. In other aspects, the resulting debris-containing fraction of an initial clarification is resuspended, treated with high salt to liberate virus from the debris, reclarified, and the resulting clarified solution added back to the original clarified solution. Thus, the volume of virus-containing solution may increase during processing.

Working with large volumes of virus-containing solution may be cumbersome, particularly when recovering virus from sucrose density gradients. Methods of reducing the volume of virus-containing solutions without significant loss of virus are known in the art. For example, the virus-containing solution may be subjected to tangential flow filtration (TFF) or diafiltration. In TFF, viruses in solution are passed through hollow fiber filter tubes or across plates of filter material. As opposed to normal flow filtration wherein the feed flow and pressure are in the same direction, TFF relies upon pressure that is perpendicular to the feed flow. Thus, in TFF, the filtrate passes through the membrane-containing walls of the tube while the retentate flows down the path of the tube. During this process, solution volume can be reduced as desired.

In certain embodiments, it may be desirable to subject a virus-containing solution to diafiltration. During diafiltration surfactants, proteins, or other solutes that freely permeate the membrane are removed from the solution. Generally, there are two common modes of diafiltration: Batch and constant-volume. During batch diafiltration, a large volume of buffer or solution is added and then the retentate is concentrated. During constant-volume diafiltration, buffer or solution is added at the same rate that the filtrate is removed.

Membranes for use in TFF or diafiltration of virus-containing solutions are commercially available (e.g., MILLIPORE, Billerica, Mass.). In preferred embodiments, the membrane cutoff range is 100 kD -0.05 μm.

In certain embodiments, the present invention can be applied to the purification of one or more proteins encoded by a virus and, in some instances, secreted into allantoic fluid by infected embryonic cells. The protein can be a viral protein or a protein encoded by a heterologous gene contained in a recombinant virus vector. In preferred embodiments, one or more salts are added to the allantoic fluid containing the protein to dissociate the protein from the debris. Alternatively, the protein associated with fibrous debris is separated from the allantoic fluid, e.g., by centrifugation or filtration, and the debris-containing fraction is then subjected to a non-isotonic salt concentration to dissociate the protein from the debris. The dissociated protein is subsequently purified using standard techniques.

When applied to the recovery of influenza viruses from chick allantoic fluid, the present invention provides a significantly reduction of the number of eggs that are required for a given influenza vaccine production run. This, in turn, reduces the possibility of vaccine shortages at the start of the annual flu season. Sundry benefits also include a smaller total workload and an easing of waste management issues. All of these benefits significantly reduce the cost of producing influenza vaccines.

In specific embodiments of the invention as applied to the extraction of influenza from allantoic fluids, the present method can be applied in the following particular manner.

Infected allantoic fluids containing high titre influenza virus vaccine strains are harvested under standard industry procedures and either processed immediately or stored in a frozen state (e.g., at −70° C.) prior to further processing.

When processed, liquid allantoic fluid is treated with an equal volume of phosphate-buffered 16-20% (w/v) NaCl at a pH usually in the range 6.5 to 8.5, depending on the strain of influenza virus to be purified, and with or without a chelating agent such as EDTA or other additives. After a suitable incubation, approximately 5 minutes or longer, where virus has dissociated from fibrous debris within the allantoic material, virus can be purified from the solution by sucrose density centrifugation. Alternatively, one or more clarification steps may be employed. In certain embodiments, the viral preparation is clarified by centrifugation at up to 14,000×g, e.g., 2,000-5,000×g. The supernatant is significantly enriched for live virus over supernatants not receiving the high-salt treatment. Pelleted debris may optionally be treated with a solution containing a high concentration of salt to extract any virus which may not have been liberated from the contaminating debris.

Alternately, the allantoic fluid may be clarified to form a clarified liquid fraction and a debris-containing fraction. Preferred methods of clarification include centrifugation and filtration. The resulting pellet or filter retentate is suspended or washed in high salt concentration solutions to liberate virus, which optionally can be pooled back into the bulk allantoic fluid with or without clarification by centrifugation or other means.

The clarity of the treated supernatant can generally facilitate further purification by sucrose density centrifugation. A step or continuous 30-50% (w/v) sucrose gradient is typically employed. Manufacturers of influenza vaccine typically use continuous flow centrifugation strategies.

Finally, live influenza virus retrieved from sucrose gradients usually has a significant proportion of the virus in an aggregated state. Further treatment of the isolated gradient fractions or fraction pools with phosphate-buffered high salt solution, or other solution of high ionic strength, at a pH usually in the range 6.5 to 8.5, liberates aggregated live influenza virus and maximizes virus yield, which can be monitored by HA titre, infectivity assay, immunoassay and electron microscopy.

The post-purification treatment of virus preparations achieves a solution of disaggregated or, ideally, monodisperse virus particles, which can be further manipulated with less loss than typically encountered. For example, formalin inactivation of gradient-purified virus is often not completely effective, due to the presence of virus aggregates, and leads to significant product loss and necessitates post-formalin processing. In the case of influenza vaccines, the presence of live virus following formalin treatment requires the application of ether extraction or other manipulation. After high-salt treatment, formalin treatment of the virus preparation is less likely to fail, and product loss due to aggregation is greatly reduced.

A further benefit of the methods of the present invention is that dissociation of virus from debris in the allantoic fluid leads to recovery of virus stocks having increased purity, i.e, containing significantly less contamination by egg components. Because egg components, such as ovalbumin, can cause an allergic reaction in certain individuals, the methods of the present invention are thought to provide for vaccines having a greater purity and, thus, have a decreased likelihood in causing an allergic reaction in an individual receiving the vaccine. For example, one or more sucrose gradient fractionations of influenza virus which has been subjected to dissociation from allantoic fluid debris by elevated salt treatment will ordinarily be sufficient to provide products having no detectable ovalbumin.

Embodiments of the present invention will be described with reference to the following examples, which are presented for illustrative purposes only and are not intended to limit the scope of the invention.

EXAMPLES

Example 1

In Influenza-Infected Allantoic Fluids, Most Virus is Present in Highly Insoluble Virus/Debris Aggregates Raw allantoic pools were assayed by HA (End-point determination) with and without clarification by centrifugation (Eppendorf microcentrifuge, 5,000 RPM for 5 minutes).

TABLE 1

| Virus Strain | Titre (HAU/mL) | |
| --- | --- | --- |
| | Untreated | Clarified |
| Flu A/New Caledonia | 2,560 | 640 |
| Flu A/Panama | 1,280 | 320 |
| Flu A/Moscow | 1,280 | 320 |
| Flu A/Texas | 10,240 | 320 |
| Flu B/Yamanashi | 2,560 | 640 |
| Flu B/Hong Kong | 1,280 | 160 |

Table 1 indicates that clarification by centrifugation typically caused a four-fold reduction in HA titer, although far higher increments were recorded (Flu A/Texas). Overall, the data show the majority of influenza present in allantoic pools is in a low solubility form, easily removed by physical manipulation.

Example 2

Treatment of Allantoic Fluids Increases Soluble Influenza Virus Titre

80 μL aliquots of virus of crude Influenza A/Moscow-infected allantoic fluid were mixed with 80 μL 3 M NaCl solution. Salt-treated virus samples and controls were incubated 15 min on ice with occasional mixing, then clarified by centrifugation (Eppendorf Microfuge, full speed, 30 seconds).

HA Assay: A 100 μL sample of each supernatant specimen was serially (2-fold) diluted by transfer of 50 μl into wells containing 50 μl phosphate buffered saline (PBS). An equal volume (50 μl) of 0.5% (v/v) chick RBC suspension was added, mixed, and allowed to settle at room temperature (1-2 hr). End point HA titre was determined for each test sample as the final well in the dilution series in which complete hemagglutination was observed.

Typically, as indicated in Table 2, a four-fold increase in HA titre was seen in salt-treated Flu A/Moscow infected allantoic fluid samples versus controls.

TABLE 2

| SAMPLE | HA End-point Titres (HA units/mL) 0.15 M NaCl | 1.6 M NaCl (final) |
|---|---|---|
| Flu A/Moscow 5.1 | 2,560 | 10,240 |
| Flu A/Moscow 5.3 | 320 | 2,560 |
| Flu A/Moscow 11.1 | 1,280 | 10,240 |
| Flu A/Moscow 11.2 | 2,560 | 10,240 |

Example 3

Treatment of Allantoic Debris Liberates Soluble Influenza Virus 1.5 M NaCl was applied to Flu A and B pools. Control samples were treated with 0.15 M NaCl, and each preparation was centrifuged for varying times to assess the amount of virus partitioning in the supernatant versus the pellet.

Each virus sample was aliquoted (2×300 μl) and mixed with 1 volume of 3 M NaCl or 0.15 M NaCl (control). Samples were mixed and aliquoted into 6×100 μl. After a 30 min incubation, samples were centrifuged at 10,000 RPM for 0, 2, 4, or 6 minutes (Eppendorf Microcentrifuge), and the 100 μl supernatants were retrieved and transferred to HA assay plates. Pellets were resuspended in 100 μl of 1.6 M NaCl, centrifuged for 2 minutes, and the pellet washes were transferred to HA assay plates.

Results are summarized in Tables 3 and 4. Values are HA endpoints expressed in HA Units/mL.

TABLE 3

| Flu B/Yamanashi | | | | |
|---|---|---|---|---|
| Centrifugation | 1.6 M NaCl | | 0.15 M NaCl | |
| Time | Supernatant | Pellet | Supernatant | Pellet |
| 0 | 2560 | — | 2560 | — |
| 2 | 1280 | 1280 | 0 | 2560 |
| 4 | 1280 | 640 | 0 | 5120 |
| 6 | 1280 | 640 | 0 | 5120 |

TABLE 4

| Flu A/Moscow | | | | |
|---|---|---|---|---|
| Centrifugation | 1.6 M NaCl | | 0.15 M NaCl | |
| Time | Supernatant | Pellet | Supernatant | Pellet |
| 0 | 2560 | — | 1280 | — |
| 2 | 2560 | 320 | 640 | 1280 |
| 4 | 2560 | 640 | 640 | 1280 |
| 6 | 2560 | 640 | 640 | 1280 |

Example 4

Treatment Greatly Increases Virus Yield in Sucrose Gradient-Purified Influenza a Virus Allantoic fluid samples for high salt treatment were clarified by centrifugation, and virus was retrieved from the debris pellet by two 10% volume 1.6 M salt washes (overnight, and then 1 hour). Washes were reclarified and then pooled back with the allantoic supernatants.

Control samples were clarified using a coarse glass fibre ‘depth’ filter, to mimic the typical process used for vaccine manufacture. Controls remained slightly cloudy after filtration. Secondary filtration, through 1 μm or 0.45 μm filters, was not employed, thereby providing a worst-case-scenario for technology-based yield gains.

Each of the allantoic preparations was fractionated on 6 mL sucrose step gradients to achieve a 17:1 loading ratio. Allantoic samples were loaded onto gradients in several steps to achieve the overall loading ratio.

TABLE 5

| Flu A/New Caledonia Gradient Loading | | | |
|---|---|---|---|
| Experiment | Salt Treated HAU | Control HAU | Recovery Ratio |
| 1 | 5,232,640 | 86,816 | 60:1 |
| 2 | 4,149,120 | 95,488 | 44:1 |

TABLE 6

Flu A/Moscow Gradient Loading

| Experiment | Salt Treated HAU | Control HAU | Recovery Ratio |
|---|---|---|---|
| 1 | 368,320 | 8,944 | 40:1 |
| 2 | 591,200 | 9,956 | 60:1 |
| 3 | 223,232 | 7,476 | 30:1 |
| 4 | 289,984 | 6,516 | 44:1 |

Figure 1:
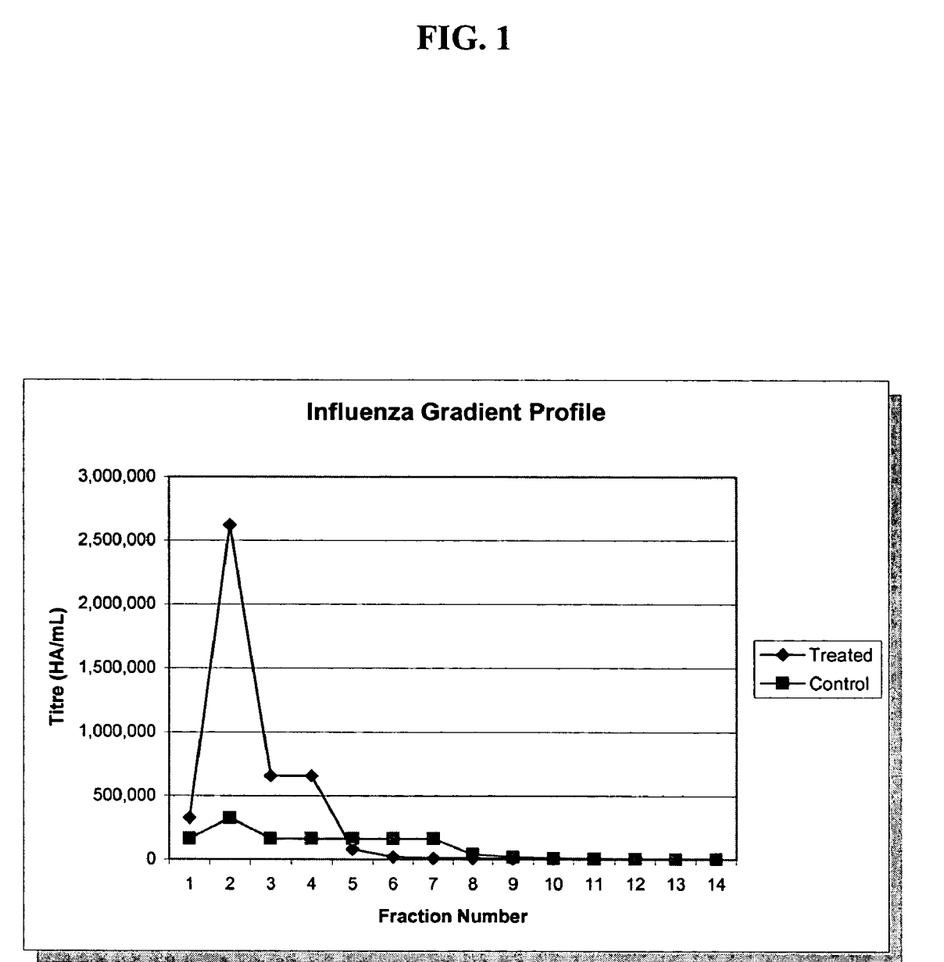
FIG. 1. Treatment of pellets from clarified allantoic fluid with a solution containing 1.6 M NaCl increases yield and provides better localization in a sucrose gradient.

In all cases, the virus peak was very sharp when high salt-treated feedstocks were used, with smaller and far broader peaks evident in the absence of this treatment. An illustrative example of a typical sucrose gradient profile, with and without treatment is given in FIG. 1.

Example 5

High-Salt Treatment Greatly Increases Virus Yield in Sucrose Gradient-Purified Influenza B Virus Samples of influenza B virus allantoic fluid were treated as in the previous example for influenza A. Control samples were again clarified using a coarse glass fibre filter. Each of the allantoic preparations was fractionated on 6 mL sucrose step gradients gradients to achieve a 17:1 loading ratio.

TABLE 7

Flu B/Hong Kong Gradient Loading

| Experiment | Salt Treated HAU | Control HAU | Recovery Ratio |
|---|---|---|---|
| 1 | 333,312 | 123,328 | 3:1 |
| 2 | 780,544 | 211,968 | 4:1 |
| 3 | 727,298 | 108,032 | 7:1 |

Example 6

High-Salt Treatment Does Not Degrade Virus Infectious Titre

Gradient-purified influenza preparations with/without high-salt treatment were assayed by $TCID_{50}$ to assess the effect of treatment on virus infectivity. Virus preparations were aliquoted, and one aliquot of each was mixed 1:1 with 3 M NaCl solution. Samples were incubated on ice for 1 hour, then clarified by centrifugation at 6,000 RPM for 5 minutes (Eppendorf Microcentrifuge). Supernatant was serially diluted in infection medium and applied to MDCK cells in 96 well assay plates. CPE and/or HA status of each well was used to score presence of infection. The method of Reed and Muench (*Amer. Jour. Hygiene*, 27: 493-497, 1938) was used to calculate infectious titres.

TABLE 8

| | Infectious Titre | |
|---|---|---|
| Virus | No Treatment | High Salt |
| Flu A/Victoria/3/75 | $1.38 \times 10^8$ PFU/mL | $1.33 \times 10^8$ PFU/mL |
| Flu A/PR/8/34 | $2.18 \times 10^4$ PFU/mL | $2.18 \times 10^4$ PFU/mL |
| Flu A/2/Japan/305/57 | $9.20 \times 10^6$ PFU/mL | $5.17 \times 10^6$ PFU/mL |
| Flu A/Hong Kong/8/68 | $2.18 \times 10^9$ PFU/mL | $1.38 \times 10^9$ PFU/mL |
| Flu A/X-31/Aichi/68 | $2.64 \times 10^8$ PFU/mL | $4.35 \times 10^7$ PFU/mL |
| Flu B/Lee/40 | $2.18 \times 10^4$ PFU/mL | $2.18 \times 10^4$ PFU/mL |

Table 8 indicates that high-salt treatment did not adversely affect the live titre of the virus strains. Thus, high-salt treatment may be applied to allantoic or other viral feedstocks without destruction of virus particles.

Example 7

Influenza Recovery Data From HA Assays, Infectious Titres and Immunoassays All Correlate Fractions of an influenza A/B pool, retrieved after sucrose gradient purification and titred by HA assay, were subjected to an optical immunoassay (OIA, Thermo BioStar).

TABLE 9

| Fraction Number | HA End-point |
|---|---|
| 9 | 32,768 |
| 10 | 131,072 |
| 11 | 524,288 |
| 12 | 1,048,576 |

Samples of each gradient fraction were diluted 1:10, 1:100, and 1:400 with PBS, then 100 μl aliquots were applied to BioStar sample tubes containing disruption agent. Assays were performed according to the Biostar kit instructions, and color intensity was graded (1-7) against a scale provided in the kit.

TABLE 10

| Gradient | Pre-Dilution | | |
|---|---|---|---|
| Fraction | 1:10 | 1:100 | 1:400 |
| 9 | 5+ | 4+ | 1+ |
| 10 | 7+ | 6+ | 2+ |
| 11 | 7+ | 6+ | 4+ |
| 12 | Out of Range | 6+ | 4+ |

Hemagglutination assays are virus/strain sensitive, but are all related to the ratio of virus particles to red blood cells. As such, HA reflects the number of virus particles in a preparation. Thermo BioStar's Flu OIA test is a rapid immunoassay which reports the presence of influenza nucleoprotein, therefore inferring the presence of virus particles. OIA color intensity results correlated with the determined HA titres.

Fractions of an influenza A/B pool, retrieved after sucrose gradient purification and titred by HA assay, were also subjected to $TCID_{50}$ assay.

TABLE 11

Comparison of HA titre and infectious titre in select gradient fractions

| Fraction | HA Titre | HA Ratio | TCID Titre | TCID Ratio |
|---|---|---|---|---|
| 5 | 256 | 1 | $1.94 \times 10^5$ | 1 |
| 14 | 524288 | 2048 | $3.73 \times 10^7$ | 192 |
| 17 | 16384 | 64 | $1.50 \times 10^7$ | 77 |

There was a correlation between the assays, in that highest HA titre corresponded to highest infectious titre, and lowest HA titre similarly had the lowest infectious titre. To facilitate comparison, a ratio of HA titre and of $TCID_{50}$ titre were calculated, relative to the lowest score measured.

Example 8

Treated Influenza Virus Remains Intact

Preliminary transmission electron microscopy (TEM) studies were performed comparing peak gradient fractions of salt-treated versus control preparations of influenza. Formvar-coated copper TEM specimen grids were floated on droplets (50 µl) of Influenza A/New Caledonia gradient fractions, and the samples adsorbed for 15 minutes at room temperature. Grids were washed twice with PBS, fixed with 0.1% glutaraldehyde in PBS (5 minutes), then washed twice using 0.2 µm-filtered WFI water and negative stained for 1 minute with 2% phosphotungstic acid. Specimens were air dried, then examined on a Hitachi H-7000 Transmission Electron Microscope using an accelerating voltage of 75 kV. Images were captured electronically in a 12-bit grayscale compressed TIF format using a Hamamatsu ORCA HR CCD camera (AMT XR-60 imaging system).

Virus particles were observed in preparations that had been treated with high salt prior to gradient fractionation, and appeared to be morphologically intact and the same as untreated controls. Virions had an intact envelope, which negative stain failed to penetrate, and prominent surface spikes. Spherical and pleomorphic virion forms were observed in both treated and control preparations.

Virions in Control preparations were often associated with debris and/or were attached to a mesh-like fibrous contaminate, which by negative stain seemed to condense around or encapsulate the virions. In contrast, virions in the salt-treated preparations were predominantly monodisperse. Moreover, in the salt-treated preparations, the nature of the contaminating fibrous matrix appeared to have changed and there was no obvious association of the fibrous matrix with the virions.

Example 9

Gradient Peak Analysis by Refractometer Indicates Virus Density is Not Altered by Treatment Gradient fractions characterized by HA analysis were concomitantly analyzed by optical refractometer to determine density corresponding to HA peak activity. A Misco Palm Abbe model PA200 was used to measure refractive index for each gradient fraction, which were in turn converted to density values using standard look-up tables for sucrose solutions.

TABLE 12

Refractive index corresponding to peak HA activity for sucrose gradient fractionation of Influenza A/Texas allantoic pools.

| | Refractive Index of Virus Peak | |
|---|---|---|
| Experiment | Salt-Treated | Control |
| Run A (FPD4.016) | 1.4020–1.4072 | 1.4038–1.4089 |
| Run B (FPD4.018) | 1.4056–1.4078 | 1.4039–1.4068 |
| Run C (FPD4.020) | 1.4059–1.4081 | 1.4074–1.4096 |

TABLE 13

Refractive index corresponding to peak HA activity for sucrose gradient fractionation of Influenza B/Hong Kong allantoic pools.

| | Refractive Index of Virus Peak | |
|---|---|---|
| Experiment | Salt-Treated | Control |
| Run A (FPD4.016) | 1.4068 | 1.4069–1.4093 |
| Run B (FPD4.018) | 1.4032–1.4086 | 1.4063 |
| Run C (FPD4.020) | 1.4079–1.4096 | 1.4079 |

Refractive index data for Influenza A/Texas and Influenza B/Hong Kong sucrose gradients are summarized in Table 12 and Table 13. For each experimental run and for both test viruses, there was close correlation of HA peak fraction density of salt-treated versus control allantoic specimens.

Example 10

Diluting Virus-Containing Allantoic Fluid Prior to Treatment Virus Yield

Each allantoic virus preparation (Influenza B/Yamanashi and Influenza A/Moscow) included four test samples (100 mL each) for gradient purification. Controls were unfiltered (Series A) or clarified through a glass fiber depth-type filter (Series B). Treated samples were prediluted by addition of 0.5 volume PBS, bringing the sample volume to 150 mL, then an equal volume (150 mL) of 20×PBS was added and incubated 1 hour overnight at 4° C. These treated samples were re-concentrated to 100 mL using a 500 kda-cutoff hollow fiber filter, and either not clarified (Series C) or clarified by low trifugation (Series D). All were subjected to sucrose gradient purification, fractionated, and assessed by HA assay.

The results are summarized in Tables 14 and 15.

TABLE 14

| | Influenza B/Yamanashi | | | |
|---|---|---|---|---|
| Fraction Number | Gradient [A]: Filtered Control Allantoic Fluid | Gradient [B]: Control Allantoic Fluid | Gradient [C]: Salt-Treated Allantoic Fluid | Gradient [D]: Salt-Treated and Filtered Allantoic Fluid |
| 1 | 5,120 | 327,680 | 20,480 | 81,920 |
| 2 | 10,240 | 163,840 | 163,840 | 81,920 |
| 3 | 163,840 | 163,840 | 335,544,320 | 81,920 |
| 4 | 655,360 | 655,360 | 5,242,880 | 2,621,440 |
| 5 | 655,360 | 327,680 | 335,544,320 | 10,485,760 |
| 6 | 655,360 | 163,840 | 41,943,040 | 2,621,440 |
| 7 | 655,360 | 81,920 | 327,680 | 163,840 |
| 8 | 327,680 | 81,920 | 40,960 | 40,960 |
| 9 | 81,920 | 40,960 | 40,960 | 20,480 |
| 10 | 81,920 | 20,480 | 20,480 | 20,480 |
| 11 | 40,960 | 10,240 | 10,240 | 10,240 |
| 12 | 40,960 | 5,120 | 10,240 | 10,240 |
| Total HA | 3,374,080 | 2,042,880 | 718,909,440 | 16,240,640 |

TABLE 15

Influenza A/Moscow

| Fraction Number | Gradient [A]: Filtered Control Allantoic Fluid | Gradient [B]: Control Allantoic Fluid | Gradient [C]: Salt-Treated Allantoic Fluid | Gradient [D]: Salt-Treated and Filtered Allantoic Fluid |
|---|---|---|---|---|
| 1 | 320 | 320 | 10,240 | 10,240 |
| 2 | 640 | 640 | 10,240 | 20,480 |
| 3 | 1,280 | 1,280 | 20,480 | 40,960 |
| 4 | 2,560 | 2,560 | 81,920 | 81,920 |
| 5 | 1,280 | 2,560 | 327,680 | 81,920 |
| 6 | 1,280 | 1,280 | 1,310,720 | 81,920 |
| 7 | 320 | 320 | 5,242,880 | 20,480 |
| 8 | 20 | 160 | 2,621,440 | 5,120 |
| 9 | 80 | 160 | 40,960 | 5,120 |
| 10 | 40 | 160 | 20,480 | 2,560 |
| 11 | 20 | 80 | 10,240 | 2,560 |
| 12 | 20 | 40 | 5,120 | 2,560 |
| Total HA | 7,860 | 9,560 | 9,702,400 | 355,840 |

Control samples yielded approximately the same amount of HA units for each test virus, regardless of whether they were clarified by filtration. The controls which were not filtered prior to gradient separation had large pellets.

In contrast, the diluted then salt-treated preparations yielded much higher HA titres than the non-treated controls. Clarification was not necessary for virus banding, and give the highest yields. Virus removed by clarification following the salt treatment was not optimally reclaimed, hence yields are lower relative to the non-clarified samples. However, significant yield improvements relative to controls were still achieved by pre-dilution and salt treatment irrespective of clarification prior to gradient separation. Table 14 indicates that, for Influenza B/Yamanashi, yields relative to the filtered control (Series A) were increased 213-fold in the test sample that lacked clarification (Series C) and 5-fold in the clarified test sample (Series D), respectively. Table 15 indicates that, for Influenza A/Moscow, yields relative to the filtered control were increased 1,234-fold in the test sample that lacked clarification and 45-fold in the clarified test sample, respectively.

It will be apparent from the prior illustrative examples of practice of the invention that recovery of virus from allantoic fluid through use of elevated salt treatment can readily be optimized by adjustments in volume/salt content so that the salt concentration will not be so high as to precipitate allantoic fluid proteins (and virus associated therewith) nor so low as to fail to optimally function in disassociation of virus from allantoic fluid debris. Such optimization procedures are readily carried out through making a preliminary analysis of the pooled allantoic fluid to be subject to salt treatment and adjusting the volume of the pooled fluid based on these initial tests. In this manner, batch-to-batch, and possibly even strain-to-strain, variations in allantoic fluid proteins are accounted for.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Likewise, while the above illustrative examples all relate to improvement of yields from allantoic fluids in which various strains of influenza A and B virus have been grown, the methods of the invention are readily applied to other enveloped viruses typically grown in the allantoic fluid of virus-infected chick embryos. Indeed, the enhanced recoveries associated with practice of the present invention are likely to render use of egg-based viral growth a method of choice for viruses now grown in mammalian cell culture provided standard adaptions of virus to such growth are performed.

The references cited herein throughout, to the extent that they provide exemplary procedural or other details supplementary to those set forth herein, are all specifically incorporated herein by reference.

We claim:

1. A process for recovering virus from debris-containing allantoic fluid of virus-infected chick embryos, comprising the steps of:
    (a) adding one or more salts to the allantoic fluid to generate a total salt concentration therein of greater than 0.5 M thereby dissociating virus from the debris; and
    (b) recovering virus dissociated from debris and solubilized in the allantoic fluid.

2. The process of claim 1, wherein the salt is added to the allantoic fluid prior to removing the allantoic fluid from an egg.

3. The process of claim 1, wherein recovery step (b) comprises clarifying the allantoic fluid of step (a) by centrifugation to form a debris-containing pellet and a virus-containing supernatant.

4. The process of claim 3, further comprising dissociating virus from the pellet by suspending the pellet into a solution having a total salt concentration of 0.5 M or greater and recovering virus from the resulting suspension.

5. The process of claim 1, wherein recovery step (b) comprises clarifying the allantoic fluid of step (a) by filtration to form a virus-containing filtrate and a debris-containing filter retentate.

6. The process of claim 1, wherein step (b) comprises sucrose density centrifugation of allantoic fluid of step a) to localize virus within the density gradient.

7. The process of claim 1, wherein the virus is an enveloped virus.

8. The process of claim 7, wherein the enveloped virus comprises an RNA genome.

9. The process of claim 8, wherein the enveloped virus is a member of a virus family selected from the group consisting of orthomyxoviridae, paramyxoviridae, flaviviridae, togaviridae, rhabdoviridae, and coronaviridae.

10. The process of claim 9, wherein the virus is an influenza virus.

11. The process of claim 10, wherein the virus is an Influenza A virus.

12. The process of claim 10, wherein the virus is an Influenza B virus.

13. The process of claim 1, comprising diluting the allantoic fluid prior to the addition of said one or more salts.

14. The process of claim 11, wherein the virus is Moscow strain of Influenza A.

15. The process of claim 1, wherein a total salt concentration from 1.0 M to 3.5 M is generated in step (a).

16. The process of claim 15, wherein said one or more salts comprise sodium chloride.

17. The process of claim 1, wherein said one or more salts are contained within a phosphate buffered solution.

18. The process of claim 1, wherein the pH of the allantoic fluid is adjusted to or maintained in the range of pH 3 to 10.

19. In a process for recovery of virus from debris-containing allantoic fluid of virus-infected chick embryos wherein the allantoic fluid is subjected to clarification to form a clarified liquid fraction and a debris-containing fraction, the improvement comprising extracting virus from both the clarified liquid fraction and the debris-containing fraction.

20. The process of claim 19, wherein said extracting step comprising:
   (a) dissociating virus associated with the debris-containing fraction into a suspension with a solution of one or more salts having a non-isotonic total salt concentration therein; and
   (b) recovering dissociated virus from the suspension.

21. The process of claim 20, wherein said extracting step comprises:
   (a) dissociating virus associated with the debris-containing fraction into a suspension with a solution of one or more salts having a total salt concentration therein of 0.5 M or greater; and
   (b) recovering dissociated virus from the suspension.

22. The process of claim 21, wherein said clarification comprises centrifugation and said debris-containing fraction comprises a centrifugation pellet.

23. The process of claim 21, wherein said clarification comprises filtration and said debris-containing fraction comprises a filter retentate.

24. The process of claim 21, further comprising the step of recovering virus from the suspension by clarifying the suspension to form a second clarified liquid and a second debris-containing fraction.

25. The process of claim 24, further comprising the step of recovering virus from the second clarified fluid by localization on a sucrose density gradient.

26. The process of claim 21, wherein the virus is an enveloped virus.

27. The process of claim 26, wherein the enveloped virus comprises an RNA genome.

28. The process of claim 27, wherein the enveloped virus is a member of a virus family selected from the group consisting of orthomyxoviridae, paramyxoviridae, flaviviridae, togaviridae, rhabdoviridae, and coronaviridae.

29. The process of claim 28, wherein the virus is an Influenza virus.

30. The process of claim 29, wherein the virus is an Influenza A virus.

31. The process of claim 29, wherein the virus is an Influenza B virus.

32. The process of claim 21, comprising diluting the allantoic fluid prior to the addition of said one or more salts.

33. The process of claim 30, wherein the virus is Moscow strain of Influenza A.

34. The process of claim 21, wherein said total salt concentration in said suspension is from 1.0 M to 3.5 M.

35. The process of claim 34, wherein said one or more salts comprise sodium chloride.

36. The process of claim 21, wherein the pH of the allantoic fluid is adjusted to or maintained in the range of pH 3 to 10.

37. A process for recovering influenza virus from debris-containing allantoic fluid of virus-infected chick embryos comprising the steps of:
   a) adding one or more salts to the allantoic fluid to generate a total salt concentration therein of 1.0 M or greater thereby dissociating virus from the debris;
   b) clarifying the allantoic fluid by centrifugation or filtration;
   c) subjecting clarified allantoic fluid to sucrose density gradient separation to localize virus within the density gradient; and
   d) isolating localized virus from the gradient.

38. The process according to claim 37, wherein the allantoic fluid of step a) has a pH adjusted to or maintained in the range pH 3.0 to pH 6.8.

39. The process according to claim 37, wherein the allantoic fluid of step a) has a pH adjusted to or maintained in the range pH 6.8 to pH 9.8.

40. The process according to claim 37 further comprising suspending the pellet resulting from centrifugation or retentate resulting from filtration in a salt solution providing a total salt concentration of 1.0 M or greater.

* * * * *